(12) United States Patent
Chada et al.

(10) Patent No.: US 7,419,951 B2
(45) Date of Patent: Sep. 2, 2008

(54) METHOD OF REDUCING ADIPOCYTE GROWTH IN A SUBJECT IN NEED THEREOF BY ADMINISTRATION OF NATRIURETIC PEPTIDE RECEPTOR C INHIBITORS

(75) Inventors: Kiran K. Chada, New York, NY (US); Roland Chouinard, Piscataway, NJ (US); Hena Ashar, Edison, NY (US); Abu Sayed, Cincinnati, OH (US)

(73) Assignee: HMGene Inc., Piscataway, NJ (US)

( * ) Notice: Subject to any disclaimer, the term of this patent is extended or adjusted under 35 U.S.C. 154(b) by 424 days.

(21) Appl. No.: 10/898,490

(22) Filed: Jul. 22, 2004

(65) Prior Publication Data

US 2005/0065092 A1    Mar. 24, 2005

Related U.S. Application Data

(63) Continuation-in-part of application No. 10/768,566, filed on Jan. 29, 2004, and a continuation-in-part of application No. 10/630,423, filed on Jul. 29, 2003.

(60) Provisional application No. 60/478,206, filed on Jun. 12, 2003, provisional application No. 60/398,785, filed on Jul. 29, 2002.

(51) Int. Cl.
*A61K 38/00* (2006.01)
*C07K 5/00* (2006.01)

(52) U.S. Cl. ............................ 514/2; 530/300; 530/324; 514/909

(58) Field of Classification Search ................... None
See application file for complete search history.

(56) References Cited

OTHER PUBLICATIONS

Matsukawa et al., Proc. Natl. Acad. Sci. USA 96: 7403-7408, 1999.*
Sun et al., Am J. Phys. Renal Phys. 282 : 220-227, 2002.*
Campese et al Hypertension 28: 335-340, 1996.*
Rebbeck et al., Nature Review Genetics 5: 589-97, 2004.*
Flier et al., "Leptin Expression and action: New experimental paradigms", PNAS, vol. 94, pp. 4242-4245 (Apr. 1997).
Samad et al., "Tissue factor gene expression in the adipose tissues of obese mice", Proc. Natl. Acad. Sci. USA, vol. 95, pp. 7591-7596 (Jun. 1998).

* cited by examiner

*Primary Examiner*—Robert Landsman
*Assistant Examiner*—Gyan Chandra
(74) *Attorney, Agent, or Firm*—Gary J. Gershik; Cooper & Dunham LLP

(57) ABSTRACT

Disclosed is a method of using synthetic analogs of natriuretic peptides and more particularly to synthetic linear peptide analogs as pro-lipolytic, as anti-obesity agents, and as intermediates for or modulators of such useful compounds. Inhibitors to nprC are disclosed to treat or prevent adipose accumulation in mammals.

13 Claims, No Drawings

METHOD OF REDUCING ADIPOCYTE GROWTH IN A SUBJECT IN NEED THEREOF BY ADMINISTRATION OF NATRIURETIC PEPTIDE RECEPTOR C INHIBITORS

This application is a continuation-in-part of U.S. Ser. No. 10/768,566, filed Jan. 29, 2004, and of U.S. Ser. No. 10/630,423, filed Jul. 29, 2003, which claims benefit of U.S. Provisional Application No. 60/398,785, filed Jul. 29, 2002, and U.S. Provisional Application No. 60/478,206, filed Jun. 12, 2003, the contents of all of which are hereby incorporated by reference.

Throughout this document various publications or patents are referenced to describe the state of the art to which the invention pertains. Each of the referenced publications and patents is incorporated by reference herein.

FIELD OF THE INVENTION

The present invention relates to the field of molecular biology, human metabolism and physiology. In particular, this invention provides inhibitors of the natriuretic peptide receptor C (nprC) and methods of administration of such inhibitors to a subject for the treatment of obesity and other metabolic disorders related to an overabundance of adipose tissue.

BACKGROUND OF THE INVENTION

Obesity, or an excess of body fat relative to lean body mass, is a serious health problem in the United States and abroad. A person is clinically obese if he or she has excess adipose tissue. More particularly, for purposes of the present invention, a person is obese if the person's body mass index equals or exceeds 27 $kg/m^2$ and the person has excess adipose tissue.

Statistics suggest that more than 25% of the United States population and 27% of the Canadian population are overweight. Complications of obesity include, among others, diabetes mellitus, hypertension, hyperlipoproteinemia, cardiac diseases (atherosclerotic disease, congestive heart failure, etc.), pulmonary diseases (e.g., sleep apnea, restrictive lung disease), cerebrovascular injury, cancers (including breast, uterine, colon, and prostate), gall bladder disease (stones, infection), toxemia during pregnancy, risks during surgery (e.g., pneumonia, wound infection, thrombo-phlebitis), gout, decreased fertility, degenerative arthritis, and early mortality. Psychological complications of obesity include poor self-image and poor body-image. Social complications of obesity include discrimination in jobs, education and marriage. Despite the known associated risks, a significant portion of the population is unable to lose weight or maintain weight loss. Obesity is now considered the second leading cause of preventable death in the United States, second only to smoking, with an estimated 300,000 deaths annually. Accordingly, reduction of the prevalence of obesity in the adult population to less than 20% is included by the US Department of Health and Human Services among the national health objectives.

The human tragedy notwithstanding, the monetary costs of obesity are staggering. The total cost attributable to obesity in 1995 has been estimated to be in excess of $99 billion, with approximately $51.64 billion paid in direct medical costs. Overall, the direct costs associated with obesity represent 5.7% of the annual United States national health expenditure. Thus, it is clear that the magnitude of this problem produces a significant demand for safe and effective treatments for obesity. Obesity has a number of known and suspected etiologies. See A. Sclafani, "Animal Models of Obesity: Classification and Characterization," Int. J. Obesity 8, 491-508 (1984); G. A. Bray, "Classification and Evaluation of the Obesities," Med. Clin. N. Am. 73, 161-184 (1989). While it is generally known that overeating and inactivity are factors that lead to obesity, there is substantial evidence of genetic contribution to obesity. Although the molecular characterization of genetic pathways associated with obesity is incomplete, several recent advances into the elucidation of these pathways have been made. Research indicates that there are several genes that act independently or in combination to modulate metabolic pathways associated with excess adipose tissue accumulation. The presence of these various pathways suggests a complex system of obesity regulation, a system that has not yet been fully defined.

Some mouse models for obesity include obese (ob/ob), agouti (Ay/a), tubby (tub), fat (fa/fa) and diabetes (db/db). These models have proven to be effective in the molecular characterization of these genetic loci because of their ability to simplify the heritability of complex traits.

One gene responsible for the autosomal recessive mouse obesity mutation tub has been identified by positional cloning and shown to be associated with maturity-onset obesity (U.S. Pat. No. 5,776,762). Identification of the tub gene and the protein it encodes may lead to the development of agents that will function to modulate either the protein or gene expression. However, a disadvantage of this system is the ubiquitous nature of the gene, in that the gene is expressed in high levels in the brain, eye and testis, and at lower levels in various adult and fetal tissues, including small and large intestine, ovary and adipose tissue. Although the gene may be used as a probe for identification of other tubby polypeptides, development of agents to modulate the expression of these polypeptides would not be specific to a particular tissue.

Similarly, the ob gene has recently been cloned. The ob gene encodes a protein known as leptin, which has been implicated in an energy feedback loop responsible for controlling vertebrate energy balance. Serum levels of leptin are increased proportionately to excess adipose accumulation as a result of increased expression in hypertrophic fat cells in obese patients. In vitro studies have indicated that insulin and glucocorticoids upregulate leptin mRNA expression in a synergistic manner. The subsequent expression of the protein product thereby functions to stimulate metabolic activity. The promoter of the ob gene has been cloned and is a candidate for pharmacological control (U.S. Pat. No. 6,124,448).

In addition to cloning the promoter of the ob gene, attempts at obesity regulation have also been made through modulation of the ob gene. The ob/ob mouse is a model of obesity and diabetes that carries an autosomal recessive trait linked to a mutation in the sixth chromosome (Yiying Zhang et al. Nature 372: 425-32 (1994). Pharmacological agents have therefore been developed to mimic the action of the ob gene encoded protein and assist in regulation of appetite and metabolism. However, the majority of obese humans actually have normal or somewhat elevated levels of leptin as compared to lean humans leading some to hypothesize that human obesity may be more related to leptin resistance rather than leptin deficiency. Recent clinical trials have shown that leptin may be useful for a certain subset of patients, but not for the treatment of obesity generally (Gura, T., Science 1999, 286 (5441): 881-2).

Using molecular and classical genetic markers, the ob and db genes have been mapped to proximal chromosome 6 and midchromosome 4, respectively (Bahary et al., Proc. Nat. Acad. Sci. USA, 87:8642-8646 (1990); Friedman et al., Genomics, 11:1054-1062 (1991)). In both cases, the mutations map to regions of the mouse genome that are syntenic with human, which suggested that if there were human homologs of ob and db, they would likely map, respectively, to human chromosomes 7q and 1p. In fact, the human homologs have been positionally cloned—OB (the human homolog for ob) has been cloned to human chromosome 7q31.3 (Isse, et al. *J Biol Chem* 1995 Nov. 17; 270 (46): 27728-33). LEPR (the human homolog for db) has been mapped to human chromosome 1p31 (Thompson, et al. *Genomics* 1997; 39(2):227-30). Defects in the leptin receptor gene results in obesity in other mammalian species: the fa gene in the rat encodes the leptin receptor.

Further, a method for detecting differential expression of specific gene loci has been suggested as a method for identifying a compound that modulates gene expression, but specific proteins and pathways have not yet been identified.

Traditionally, pharmacological approaches to weight loss or prevention of weight gain have relied either on reduction of food intake or on reduction of nutrient absorption. Drugs of the first group, which include Redux (American Home Products) and Meridia (Knoll Pharmaceuticals), affect neurotransmitter activity in the brain, resulting in appetite suppression and decreased food intake. While effective in producing a moderate weight loss in some proportion of patients these medications are associated with a number of adverse side effects.

Drugs of the second group, including Xenical (Hoffmann-La Roche), reduce total absorption of fat from the gastrointestinal tract. However, inhibition of fat absorption by this drug can lead to avitaminosis since successful uptake of fat soluble vitamins from the intestines is impaired in the absence of fat. Additionally, these drugs produce unpleasant side-effects, such as steatorrhea, which reduce patient compliance. Other health problems have been shown to stem directly or indirectly from use of the drug as well such as an increased incidence of breast cancer.

Consequently, focus has since shifted away from these group one and two pharmaceuticals and instead towards targeting suppression of gene expression or protein inhibition. Some pharmaceutical examples are leptin (Amgen), leptin receptor (Progenitor) and tubby (Millennium Pharmaceuticals). However, expression of these genes is not limited to adipose tissue and many specifically act on the brain to stimulate or decrease adipose accumulation. Therefore, it is possible that development of drugs to specifically target the central nervous system (CNS) to interfere with the CNS-active pathways in obese patients may produce similar side effects to those appetite suppressors that are currently available. Thus, it is extremely beneficial to target adipose specific genes or the proteins encoded by such genes. Moreover, treating obese or overweight subjects with compounds that target genes or the proteins they encode that regulate the ability of the adipocyte to store fat will result in a decrease in adipose mass and a positive impact on the subject's health. The natriuretic peptide clearance receptor represents one such gene/protein.

The natriuretic peptide (NP) system is an important component in the regulation of sodium and water balance, blood volume and blood pressure. This system works through several mechanisms, for example decreasing renin release and consequently aldosterone release by the adrenal cortex, thereby decreasing sodium and fluid retention in the kidneys. The NP system has also been shown to inhibit vasopressin, again causing a decrease in fluid retention in the kidney. These actions contribute to reductions in blood volume, and therefore central venous pressure, cardiac output, and arterial blood pressure. A third mechanism appears to be arterial vasodilation in response to hypervolemia.

The family of natriuretic peptides includes atrial natriuretic peptide (ANP), brain natriuretic peptide (BNP) and C-type natriuretic peptide (CNP). The primary signaling molecules for these peptides are natriuretic peptide receptor A (nprA, npr1) which binds ANP and BNP, and natriuretic peptide receptor B (nprB, npr2) which binds CNP. The A and B receptors share approximately 62% identity at the amino acid level and have been classified as guanylyl cyclase receptors. That is, their intracellular domains possess a kinase-like domain and a guanylyl cyclase catalytic domain. Upon ligand binding to the extracellular ligand binding domain, the guanylyl cyclase catalytic domain is activated causing and increase in intracellular cyclic GMP (cGMP) which potentiates the physiological activity of the receptors. The A receptor has been implicated in vasodilation, increased diuresis and natriuresis, and decreased renin and aldosterone. The B receptor has been implicated in vasodilation and increased long bone growth. (for review see Levin, et al., New England Journal of Medicine 339(5): 321-328 (1998) and Potter, et al., J. Biol. Chem. 276(9): 6057-6060 (2001)).

There is a third receptor, natriuretic peptide receptor C, (nprC, npr3) which shares only approximately 32% identity with nprA and nprB over the length of the protein. The C receptor retains a similar extracellular ligand binding domain and trans-membrane domain, but has only a short intracellular domain (37 amino acid residues) which lacks both the kinase-like domain and guanylyl cyclase activation domain. ANP, BNP, and CNP all bind this receptor with approximately equal affinity. The receptor is called the natriuretic peptide clearance receptor in that it has been shown to participate in the local clearance of the natriuretic peptides. The receptor binds the ligand and is internalized. The ligand is degraded and the receptor is retroendocytozed back to the cell surface (Nussenzveig, et al., J. Biol. Chem. 265(34) 20952-20958 (1990). The C receptor accounts for approximately 50% of natriuretic peptide clearance, the other half being carried out by cell surface neutral endopeptidases. However, while nprA and nprB are often called biologically active receptors to the exclusion of nprC, it has been suggested that nprC has other biological activity other than simply natriuretic peptide clearance. Several groups have shown that the c-terminal domain of nprC can interact with inhibitory G-proteins ($G_i$) that act to downregulate adenylyl cyclase and thus reduce the level of intracellular cyclic A MP (cAMP) (Palaparti, et al., Biochem. J., 346:313-320 (2000) and Pagano, et al., J. Biol. Chem. 276(25):22064-22070 (2001)). Recently, it has been postulated that the vasodilatory effects of endothelium-derived hyperpolarizing factor (EDHF) may be attributed to such nprC mediated adenylyl cyclase inhibition (Chauhan, et al., Proc. Natl. Acad. Sci. USA, 100(3):1426-1431 (2003).

ANP and BNP have been linked to lipolysis in a cGMP dependent manner which does not depend on cAMP production or phosphodiesterase inhibition (Sengenes, et al., FASEB J., 14(10):1345-51 (2000)). Thus, ANP and BNP, but not nprC, have been implicated in the biology of the adipocyte. In this case, for example, the authors have attributed the lipolytic effects as being linked to cGMP production in which nprC does not participate.

Specific npr3 knockout mice were made to determine the effect of an absence of nprC on water balance, salt balance, and blood pressure (Matsukawa, et al., Proc. Natl. Acad. Sci. USA 96:7403-7408 (1999)). The animals have a moderately but statistically significantly lowered blood pressure and with age show an increase in daily water uptake with a significant increase in urinary output. The knockout mice also have a defect in the ability to concentrate their urine. The observed alterations in renal function were interpreted as being the result of a failure of local clearance of natriuretic peptides in the glomerular and post-glomerular structures resulting in an increase in filtered volume and a decrease in water reabsorption. The decrease in blood pressure was attributed to simple hypovolemia. These animals exhibit skeletal abnormalities including an overgrowth of the long bones as well as other defects. The authors note that the animals exhibit "elongated femurs, tibias, metatarsal, and digital bones, longer vertebral bodies, increased body length, and decreased weight [emphasis added]." However, the authors did not account for the decrease in weight nor did they make any examination of the adipose tissue.

Several spontaneously occurring mutants in the npr3 have been identified, the first of which was called longjohn (lgj) due to the skeletal defects described above. A French group studied them to examine and compare the skeletal defects among the three strains (Jaubert, et al., Proc. Natl. Acad. Sci. USA 96:10278-10283 (1999)). The authors note offhandedly that " . . . older mutant mice are exceptionally thin and at necropsy normal body fat deposits are absent." Again, the authors did not make any more mention of the animals' weight or adipose tissue.

SUMMARY OF THE INVENTION

The present invention is directed to the use of synthetic analogs of natriuretic peptides and more particularly to synthetic linear peptide analogs as pro-lipolytic or anti-obesity agents or as intermediates for or modulators of such useful compounds. Inhibitors to nprC are useful to treat or prevent adipose accumulation. A group of such inhibitors has been disclosed in PCT International Publication No. WO 00/61631, the contents of which are hereby incorporated by reference. The role of nprC in adipose biology is unclear. One possibility is this: since ANP and BNP have been shown to promote lipolysis, the lack of the clearance receptor i.e. nprC causes an increased half-life of ANP and BNP and therefore results in increased lipolysis. No alterations in weight gain have been noted in patients receiving recombinant human BNP for acute congestive heart failure, but these patients receive the medication as a bolus and thus there is likely not enough time to see an effect on adipose mass.

A series of lactams of the generic structure shown below act as nprC antagonists:

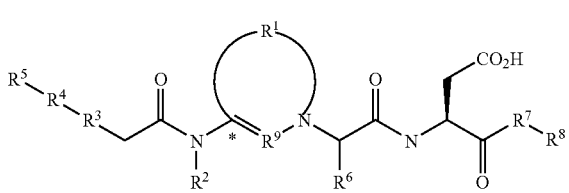

Such a replacement group contains a chiral center at the lactam α-carbon, giving the diasteriomeric pair I and II. The R-isomer of the lactam is preferred, as shown in the structures below:

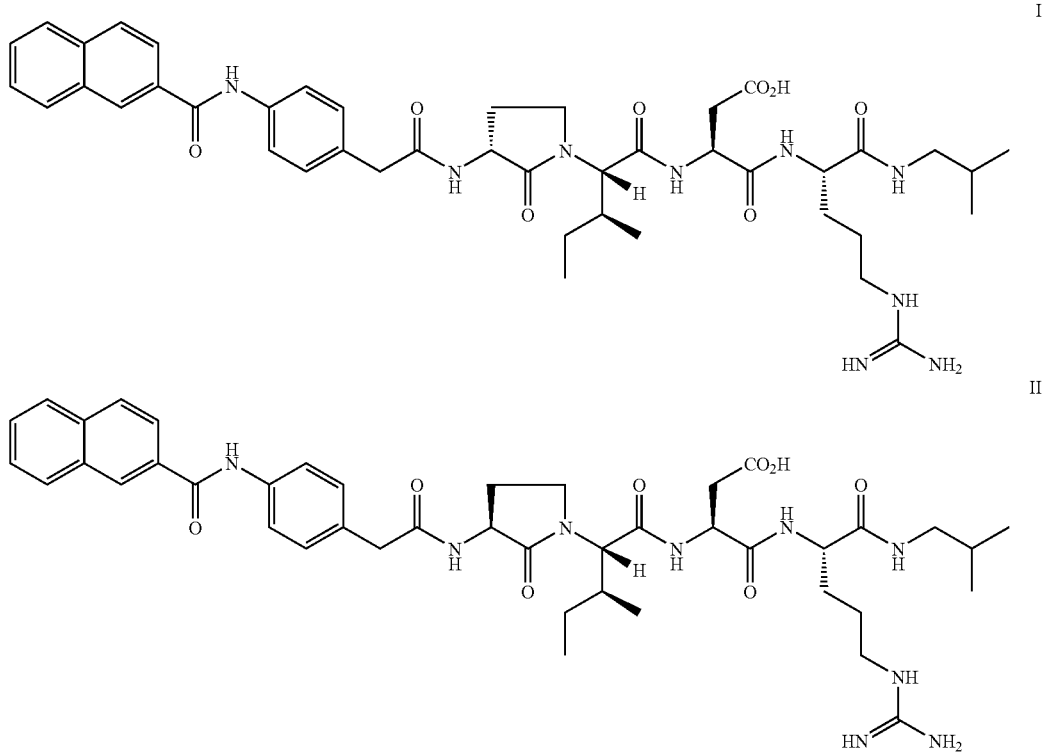

Lactam molecules containing a D-amino acid or a sarcosine residue in position $R^7$ have good metabolic stability, whereas the natural hormone ANP has poor metabolic stability. Decreases in molecular weight in the n-Cap region result in large decreases in potency. For example, truncation to the phenylacetic carboxamide (III) results in complete loss of binding affinity, while truncation of the naphthyl group to a series of substituted benzamides generally produces compounds that bind in the 100 nM range.

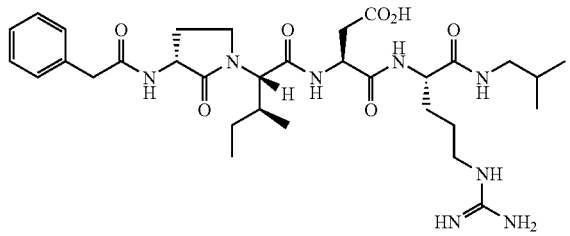

III

Heterocyclic replacements of the naphtyl group result in compounds with promising activity. A compound combining a 2-quinoxalazine as a replacement for the naphthyl ring coupled with a D-Arg-14 residue (IV) exhibits oral activity.

aromatic ring containing from zero-to-eight carbon atoms and zero-to-three heteroatoms;

$R^3$ is preferably —$CH_2CH_2CH_2$—, —(E)—CH=CHC(=O)NH—, —$CH_2CH_2C$(=O)NH—, para-disubstituted phenyl, ortho-disubstituted phenyl, meta-disubstituted phenyl or a single bond, wherein, in the disubstituted phenyl groups, one substituent is $R^4$ and the other is the methylene group alpha to the amide carbonyl, as shown in the generic structure above; $R^4$ is —NHC(=O)—, —C(=O)NH— or —S(=O),NH—;

$R^5$ is a substituted or unsubstituted alkylaryl, aryl or heteroaryl compound, preferably 1-naphthyl, 2-naphthyl, —$CH_2CH_2NHCH_2CH$=CH phenyl, —$CH_2CH_2$-phenyl, —CH=CH— phenyl, 2-quinolyl, 3-quinolyl, 4-quinolyl, 6-quinolyl, 3-isoquinolyl, 2-quinoxaline, 5-chloro-2-indolyl, 2-indolyl, 4-chlorophenyl, 4-methylphenyl, 3-methoxyphenyl, 4-cyanophenyl, 3,4-difluorophenyl, 3-chloro-4-fluorophenyl, 2,4 dichlorophenyl, 3,4-dichlorophenyl, 4-chlorophenyl, 3,5-dimethoxyphenyl, 4-tert-butylphenyl, phenyl, 4-trifluoromethylphenyl, —$CH_2CH_2CH_2$-phenyl, 6-quinolyl-C(=O)—, 2-quinoxaline-C(=O)—, 5-chloro-2-benimidazolyl, fluorenylmethoxycarbonyl,

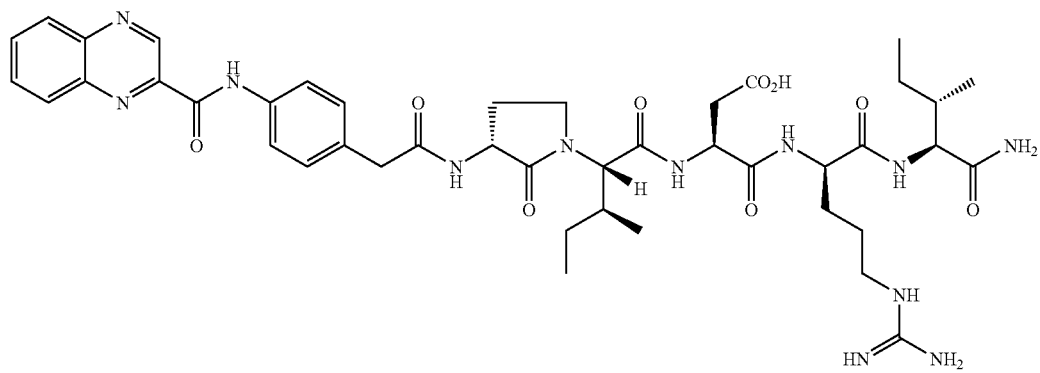

IV

DETAILED DESCRIPTION OF THE INVENTION

The instant invention calls for the use of antagonists of the natriuretic peptide clearance receptor, nprC for the treatment of overweight and obesity and the complications arising from overweight and obesity including but not limited to diabetes, atherosclerosis, coronary artery disease, cerebrovascular accident, transient ischemic accident, and cancer. The compounds to be used have the structure:

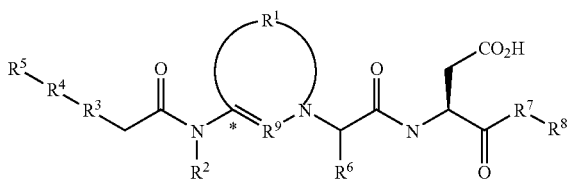

In this structure:

$R^1$ is a hydrocarbon chain containing from one to four carbon atoms and zero-to-two heteroatoms, but is preferably —$CH_2CH_2$—, —$CH_2CH_2CH_2$—, =CH—CH=CH— or —N=CH—;

$R^2$ should be hydrogen or a $C_1$-$C_4$ alkyl group, but is preferably hydrogen or methyl. $R^3$ is a zero-to-four atom chain or 4-chlorobenzyl, 4-methylbenzyl, 3-quinoxalinyl, 3,4-difluorophenyl, or 4-fluorophenyl;

$R^6$ is a $C_3$-$C_5$ branched or unbranched alkyl group, preferably isobutyl or sec-butyl;

$R_7$ is a natural or unnatural amino acid, preferably N-methylglycine, —NHCH$_2$CH$_2$NHC(=O)—, L-arginine, D-arginine, L-ornithine, D-ornithine, histidine, citrulline, proline, hydroxyproline, 3-pyridinylalanine, L-N-methylalanine, D-N-methylalanine, aminobutyric acid, or thiazolidine;

$R^8$ is L-isoleucine-NH$_2$ D-isoleucine-NH$_2$—CH$_2$-cyclopentyl, —CH$_2$-2-tetrahydrofuranyl, tert-butylglycine-NH$_2$, n-butyl, NH-cyclopentyl, NHCH$_2$-2-furanyl, —NHCH$_2$-pyrininyl, —NHCH$_2$ cyclohexyl, —NH-2-indolizidinyl, D-leucinol, —NH-isobutyl, 1-allo-isoleucine-NH$_2$, 1-hydroxycycloleucinol, 2-(aminomethyl)-1-ethyl-pyrollidine, or (S)—NH-2-methylbutyl, but if $R^7$ is —NH-2-indolizidine, then $R^8$ is absent; and $R^9$ is a one carbon spacer that is preferably =CH— or —C(=O)—; such that when $R^9$ is =CH—, then ═══ is a double bond, and when $R^9$ is —C(=O)— then ═══ is a single bond, and when $R^1$ is —N=CH— and $R^9$ is =CH—, then the central ring is a disubstituted imidazole.

Representative compounds according to the present invention include those of the structure:

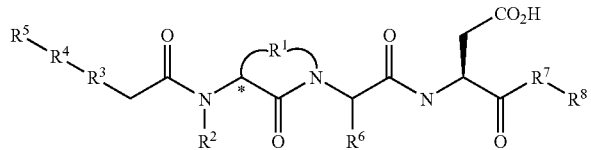

| # | R¹ | R² | R³ | R⁴ | R⁵ |
|---|----|----|----|----|----|
| 1 | (R)—CH₂CH₂— | H | para-phenyl | —C(=O)NH— | 2-naphthyl |
| 2 | (R)—CH₂CH₂— | H | para-phenyl | —C(=O)NH— | 2-naphthyl |
| 3 | (R)—CH₂CH₂— | H | para-phenyl | —C(=O)NH— | 2-naphthyl |
| 4 | (R)—CH₂CH₂— | H | a single bond | —C(=O)NH— | (E)—PhHC=CHCH₂NHCH₂CH₂— |
| 5 | (R)—CH₂CH₂— | Me | para-phenyl | —C(=O)NH— | 2-naphthyl |
| 6 | (R)—CH₂CH₂— | Me | 1,3-propyl | —NHC(=O)— | PhCH₂CH₂CH₂— |
| 7 | (R)—CH₂CH₂— | Me | —CH₂CH₂C(=O)NH— | —S(=O)₂NH— | 2-naphthyl |
| 8 | (R)—CH₂CH₂— | Me | —CH₂CH₂C(=O)NH— | —S(=O)₂NH— | (E)PhHC=CH— |
| 9 | (R)—CH₂CH₂— | Me | —CH₂CH₂C(=O)NH— | —C(=O)NH— | 6-quinolynyl-C(=O)— |
| 10 | (R)—CH₂CH₂— | Me | para-phenyl | —C(=O)NH— | 6-quinolynyl-C(=O)— |
| 11 | (R)—CH₂CH₂— | Me | para-phenyl | —C(=O)NH— | 2-quinoxalinyl-C(=O)— |
| 12 | =CH—CH=CH— | H | para-phenyl | —C(=O)NH— | 2-naphthyl |
| 13 | =CH—CH=CH— | H | para-phenyl | —C(=O)NH— | 2-naphthyl |
| 14 | =CH—CH=CH— | H | para-phenyl | —C(=O)NH— | 5-chloro-2-indolyl |
| 15 | =CH—CH=CH— | H | para-phenyl | —C(=O)NH— | 5-chloro-2-indolyl |
| 16 | (R)—CH₂CH₂— | Me | —CH₂CH₂C(=O)NH— | —C(=O)NH— | (E)PhHC=CH— |
| 17 | =CH—CH=CH— | H | para-phenyl | —C(=O)NH— | 2-naphthyl |
| 18 | =CH—CH=CH— | H | para-phenyl | —C(=O)NH— | 2-naphthyl |
| 19 | (R)—CH₂CH₂— | Me | —CH₂CH₂C(=O)NH— | —C(=O)NH— | 2-indole |
| 20 | imidazole* | H | para-phenyl | —C(=O)NH— | 2-naphthyl |
| 21 | (R)—CH₂CH₂— | Me | para-phenyl | —C(=O)NH— | 2-naphthyl |
| 22 | (R)—CH₂CH₂— | Me | —CH₂CH₂C(=O)NH— | —C(=O)NH— | (E)PhHC=CH— |
| 23 | (R)—CH₂CH₂— | Me | para-phenyl | —C(=O)NH— | 2-naphthyl |
| 24 | (R)—CH₂CH₂— | Me | para-phenyl | —C(=O)NH— | 2-naphthyl |
| 25 | (R)—CH₂CH₂— | Me | para-phenyl | —C(=O)NH— | 6-quinolynyl |
| 26 | (R)—CH₂CH₂— | Me | para-phenyl | —C(=O)NH— | 3-quinolynyl |
| 27 | (R)—CH₂CH₂— | Me | para-phenyl | —C(=O)NH— | 2-quinolynyl |
| 28 | (R)—CH₂CH₂— | Me | para-phenyl | —C(=O)NH— | 2-indole |
| 29 | (R)—CH₂CH₂— | Me | para-phenyl | —C(=O)NH— | (E)PhHC=CH— |
| 30 | (R)—CH₂CH₂— | Me | para-phenyl | —C(=O)NH— | 4-methylphenyl |
| 31 | (R)—CH₂CH₂— | H | para-phenyl | —NHC(=O)— | 4-chlorobenzyl |
| 32 | (R)—CH₂CH₂— | H | para-phenyl | —NHC(=O)— | 4-methylbenzyl |
| 33 | (R)—CH₂CH₂— | H | para-phenyl | —C(=O)NH— | 2-naphthyl |
| 34 | (R)—CH₂CH₂— | H | para-phenyl | —C(=O)NH— | 2-naphthyl |
| 35 | (R)—CH₂CH₂— | H | para-phenyl | —C(=O)NH— | 2-naphthyl |
| 36 | (R)—CH₂CH₂— | H | para-phenyl | —C(=O)NH— | 2-naphthyl |
| 37 | (R)—CH₂CH₂— | H | para-phenyl | —C(=O)NH— | 2-naphthyl |
| 38 | (R)—CH₂CH₂— | H | para-phenyl | —C(=O)NH— | 2-naphthyl |
| 39 | (R)—CH₂CH₂— | H | para-phenyl | —C(=O)NH— | 2-naphthyl |
| 40 | (R)—CH₂CH₂— | H | para-phenyl | —C(=O)NH— | 2-naphthyl |
| 41 | (R)—CH₂CH₂— | H | para-phenyl | —C(=O)NH— | 2-naphthyl |
| 42 | (R)—CH₂CH₂— | H | para-phenyl | —C(=O)NH— | 2-naphthyl |
| 43 | (R)—CH₂CH₂— | H | para-phenyl | —C(=O)NH— | 2-naphthyl |
| 44 | (R)—CH₂CH₂— | H | para-phenyl | —C(=O)NH— | 2-naphthyl |
| 45 | (R)—CH₂CH₂— | H | para-phenyl | —C(=O)NH— | 2-naphthyl |
| 46 | (R)—CH₂CH₂— | H | para-phenyl | —C(=O)NH— | 2-naphthyl |
| 47 | (R)—CH₂CH₂— | H | para-phenyl | —C(=O)NH— | 2-naphthyl |
| 48 | (R)—CH₂CH₂— | H | para-phenyl | —C(=O)NH— | 2-naphthyl |
| 49 | (R)—CH₂CH₂— | H | para-phenyl | —C(=O)NH— | 2-naphthyl |
| 50 | (R)—CH₂CH₂— | H | para-phenyl | —C(=O)NH— | 2-naphthyl |
| 51 | (R)—CH₂CH₂— | H | para-phenyl | —C(=O)NH— | 2-naphthyl |
| 52 | (R)—CH₂CH₂— | H | para-phenyl | —C(=O)NH— | 2-naphthyl |
| 53 | (R)—CH₂CH₂— | H | para-phenyl | —C(=O)NH— | 2-naphthyl |
| 54 | (R)—CH₂CH₂— | H | para-phenyl | —C(=O)NH— | 2-naphthyl |
| 55 | (R)—CH₂CH₂— | H | para-phenyl | —C(=O)NH— | 4-quinolynyl |
| 56 | (R)—CH₂CH₂— | H | para-phenyl | —C(=O)NH— | 6-quinolynyl |
| 57 | (R)—CH₂CH₂— | H | para-phenyl | —C(=O)NH— | 3-quinolynyl |
| 58 | (R)—CH₂CH₂— | H | para-phenyl | —C(=O)NH— | 2-naphthyl |
| 59 | (R)—CH₂CH₂— | H | para-phenyl | —C(=O)NH— | 3-quinoxalinyl |
| 60 | (R)—CH₂CH₂— | H | para-phenyl | —C(=O)NH— | 2-quinolynyl |
| 61 | (R)—CH₂CH₂— | H | para-phenyl | —C(=O)NH— | 3-quinolynyl |
| 62 | (R)—CH₂CH₂— | H | para-phenyl | —C(=O)NH— | 6-quinolynyl |
| 63 | (R)—CH₂CH₂— | H | para-phenyl | —C(=O)NH— | 3-isoquinolynyl |
| 64 | (R)—CH₂CH₂— | H | para-phenyl | —C(=O)NH— | 2-quinolynyl |
| 65 | (R)—CH₂CH₂— | H | para-phenyl | —C(=O)NH— | 2-indolyl |
| 66 | (R)—CH₂CH₂— | H | para-phenyl | —C(=O)NH— | 2-indolyl |
| 67 | (R)—CH₂CH₂— | H | para-phenyl | —C(=O)NH— | 4-chlorophenyl |
| 68 | (R)—CH₂CH₂— | H | para-phenyl | —C(=O)NH— | 4-trifluoromethylphenyl |

-continued

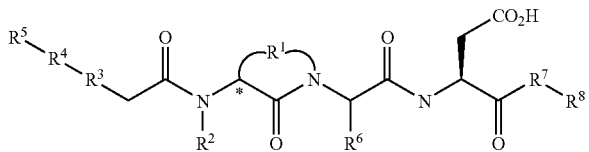

| | | | | | |
|---|---|---|---|---|---|
| 69 | (R)—CH$_2$CH$_2$— | H | para-phenyl | —C(=O)NH— | 4-fluorophenyl |
| 70 | (R)—CH$_2$CH$_2$— | H | para-phenyl | —C(=O)NH— | 4-methylphenyl |
| 71 | (R)—CH$_2$CH$_2$— | H | para-phenyl | —C(=O)NH— | 3-methoxyphenyl |
| 72 | (R)—CH$_2$CH$_2$— | H | para-phenyl | —C(=O)NH— | 4-cyanophenyl |
| 73 | (R)—CH$_2$CH$_2$— | H | para-phenyl | —C(=O)NH— | 3,4-difluorophenyl |
| 74 | (R)—CH$_2$CH$_2$— | H | para-phenyl | —C(=O)NH— | 3-chloro-4-fluorophenyl |
| 75 | (R)—CH$_2$CH$_2$— | H | para-phenyl | —C(=O)NH— | 3,5-dimethoxyphenyl |
| 76 | (R)—CH$_2$CH$_2$— | H | para-phenyl | —C(=O)NH— | 2-indolyl |
| 77 | (R)—CH$_2$CH$_2$— | H | para-phenyl | —C(=O)NH— | 3-methoxyphenyl |
| 78 | (R)—CH$_2$CH$_2$— | H | para-phenyl | —C(=O)NH— | 2,4-dichlorophenyl |
| 79 | (R)—CH$_2$CH$_2$— | H | para-phenyl | —C(=O)NH— | 4-chlorophenyl |
| 80 | (R)—CH$_2$CH$_2$— | H | para-phenyl | —C(=O)NH— | 4-chlorophenyl |
| 81 | (R)—CH$_2$CH$_2$— | H | para-phenyl | —C(=O)NH— | 4-trifluoromethylphenyl |
| 82 | (R)—CH$_2$CH$_2$— | H | para-phenyl | —C(=O)NH— | 4-chlorophenyl |
| 83 | (R)—CH$_2$CH$_2$— | H | para-phenyl | —C(=O)NH— | 4-trifluoromethylphenyl |
| 84 | (R)—CH$_2$CH$_2$— | H | para-phenyl | —C(=O)NH— | 2,4-dichlorophenyl |
| 85 | (R)—CH$_2$CH$_2$— | H | para-phenyl | —C(=O)NH— | 4-chlorophenyl |
| 86 | (R)—CH$_2$CH$_2$— | H | para-phenyl | —C(=O)NH— | 3-quinolynyl |
| 87 | (R)—CH$_2$CH$_2$— | H | para-phenyl | —C(=O)NH— | 3-quinolynyl |
| 88 | (R)—CH$_2$CH$_2$— | H | para-phenyl | —C(=O)NH— | 2-quinolynyl |
| 89 | (R)—CH$_2$CH$_2$— | H | para-phenyl | —C(=O)NH— | 3-isoquinolynyl |
| 90 | (R)—CH$_2$CH$_2$— | H | para-phenyl | —C(=O)NH— | 2-quinolynyl |
| 91 | (R)—CH$_2$CH$_2$— | H | para-phenyl | —C(=O)NH— | 2-indolyl |
| 92 | (R)—CH$_2$CH$_2$— | H | para-phenyl | —C(=O)NH— | 3-isoquinolynyl |
| 93 | (R)—CH$_2$CH$_2$— | H | para-phenyl | —C(=O)NH— | 2-indolyl |
| 94 | (R)—CH$_2$CH$_2$— | H | para-phenyl | —C(=O)NH— | 2-naphthyl |
| 95 | (R)—CH$_2$CH$_2$— | H | para-phenyl | —C(=O)NH— | 2-naphthyl |
| 96 | (R)—CH$_2$CH$_2$— | H | para-phenyl | —C(=O)NH— | 2-naphthyl |
| 97 | (R)—CH$_2$CH$_2$— | H | para-phenyl | —C(=O)NH— | 2-naphthyl |
| 98 | (R)—CH$_2$CH$_2$— | H | para-phenyl | —C(=O)NH— | 2-naphthyl |
| 99 | (R)—CH$_2$CH$_2$— | H | para-phenyl | —C(=O)NH— | 2-naphthyl |
| 100 | (R)—CH$_2$CH$_2$— | H | para-phenyl | —C(=O)NH— | 2-naphthyl |
| 101 | (R)—CH$_2$CH$_2$— | H | para-phenyl | —C(=O)NH— | 2-naphthyl |
| 102 | (R)—CH$_2$CH$_2$— | H | para-phenyl | —C(=O)NH— | 2-naphthyl |
| 103 | (R)—CH$_2$CH$_2$— | H | para-phenyl | —C(=O)NH— | 2-naphthyl |
| 104 | (R)—CH$_2$CH$_2$— | H | para-phenyl | —C(=O)NH— | 2-naphthyl |
| 105 | (S)—CH$_2$CH$_2$— | H | para-phenyl | —C(=O)NH— | 2-naphthyl |
| 106 | (R)—CH$_2$CH$_2$— | H | para-phenyl | —C(=O)NH— | 1-naphthyl |
| 107 | (R)—CH$_2$CH$_2$— | H | ortho-phenyl | —C(=O)NH— | 2-naphthyl |
| 108 | (R)—CH$_2$CH$_2$— | H | meta-phenyl | —C(=O)NH— | 1-naphthyl |
| 109 | (R)—CH$_2$CH$_2$— | H | meta-phenyl | —C(=O)NH— | 2-naphthyl |
| 110 | (R)—CH$_2$CH$_2$— | H | ortho-phenyl | —C(=O)NH— | 1-naphthyl |
| 111 | (R)—CH$_2$CH$_2$— | H | —CH$_2$CH$_2$C(=O)NH— | —NHC(=O)— | 2-phenylethyl |
| 112 | (R)—CH$_2$CH$_2$— | H | —(E)—HC=CHC(=O)NH— | —NHC(=O)— | 2-phenylethyl |
| 113 | (R)—CH$_2$CH$_2$— | H | —CH$_2$CH$_2$C(=O)NH— | —NHC(=O)— | (E)PhHC=CH— |
| 114 | (S)—CH$_2$CH$_2$— | H | para-phenyl | —C(=O)NH— | 1-naphthyl |
| 115 | (S)—CH$_2$CH$_2$— | H | ortho-phenyl | —C(=O)NH— | 2-naphthyl |
| 116 | (S)—CH$_2$CH$_2$— | H | meta-phenyl | —C(=O)NH— | 1-naphthyl |
| 117 | (S)—CH$_2$CH$_2$— | H | meta-phenyl | —C(=O)NH— | 2-naphthyl |
| 118 | (S)—CH$_2$CH$_2$— | H | —CH$_2$CH$_2$C(=O)NH— | —C(=O)NH— | (E)PhHC=CH— |
| 119 | (R)—CH$_2$CH$_2$— | H | para-phenyl | —C(=O)NH— | 2-naphthyl |
| 120 | (R)—CH$_2$CH$_2$— | H | para-phenyl | —C(=O)NH— | 2-naphthyl |
| 121 | (R)—CH$_2$CH$_2$— | H | para-phenyl | —C(=O)NH— | 2-naphthyl |
| 122 | (R)—CH$_2$CH$_2$— | H | para-phenyl | —C(=O)NH— | 2-naphthyl |
| 123 | (R)—CH$_2$CH$_2$— | H | para-phenyl | —C(=O)NH— | 2-naphthyl |
| 124 | (R)—CH$_2$CH$_2$— | H | —CH$_2$CH$_2$C(=O)NH— | —C(=O)NH— | (E)PhHC=CH— |
| 125 | (R)—CH$_2$CH$_2$— | H | para-phenyl | —C(=O)NH— | FMOC |
| 126 | (R)—CH$_2$CH$_2$— | H | para-phenyl | —C(=O)NH— | 5-chloro-2-indolyl |
| 127 | (R)—CH$_2$CH$_2$— | H | para-phenyl | —C(=O)NH— | 5-chloro-2-indolyl |
| 128 | (R)—CH$_2$CH$_2$— | H | para-phenyl | —C(=O)NH— | 5-chloro-2-indolyl |
| 129 | (R)—CH$_2$CH$_2$— | H | para-phenyl | —C(=O)NH— | 5-chloro-2-indolyl |
| 130 | (R)—CH$_2$CH$_2$— | H | para-phenyl | —C(=O)NH— | 5-chloro-2-indolyl |
| 131 | (R)—CH$_2$CH$_2$— | H | para-phenyl | —C(=O)NH— | 5-chloro-2-indolyl |
| 132 | (R)—CH$_2$CH$_2$— | H | para-phenyl | —C(=O)NH— | 6-methyl-3-pyridinyl |
| 133 | (R)—CH$_2$CH$_2$— | H | para-phenyl | —C(=O)NH— | 6-methyl-3-pyridinyl |
| 134 | (R)—CH$_2$CH$_2$— | H | para-phenyl | —C(=O)NH— | 6-quinolynyl |
| 135 | (R)—CH$_2$CH$_2$— | H | para-phenyl | —C(=O)NH— | 6-quinolynyl |
| 136 | (R)—CH$_2$CH$_2$— | H | para-phenyl | —C(=O)NH— | 3-quinoxalinyl |
| 137 | (R)—CH$_2$CH$_2$— | H | para-phenyl | —C(=O)NH— | 3-quinoxalinyl |
| 138 | (R)—CH$_2$CH$_2$— | H | para-phenyl | —C(=O)NH— | 5-chloro-2-benzimidazolyl |

-continued

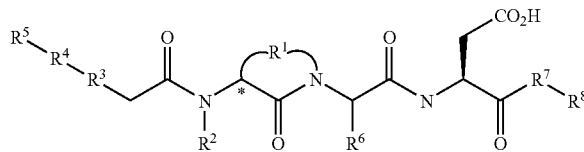

| # | | | R⁶ | R⁷ | | R⁸ |
|---|---|---|---|---|---|---|
| 139 | (R)—CH₂CH₂— | H | para-phenyl | —C(=O)NH— | 5-chloro-2-benzimidazolyl |
| 140 | (R)—CH₂CH₂— | H | para-phenyl | —C(=O)NH— | 5-chloro-2-benzimidazolyl |
| 141 | (R)—CH₂CH₂— | H | para-phenyl | —C(=O)NH— | 3-quinolynyl |
| 142 | (R)—CH₂CH₂— | H | para-phenyl | —C(=O)NH— | 3-isoquinolynyl |
| 143 | (R)—CH₂CH₂— | H | para-phenyl | —C(=O)NH— | 2-quinolynyl |
| 144 | (R)—CH₂CH₂— | H | para-phenyl | —C(=O)NH— | 2-indolyl |
| 145 | (R)—CH₂CH₂— | H | para-phenyl | —C(=O)NH— | 3-quinolynyl |
| 146 | (R)—CH₂CH₂— | H | para-phenyl | —C(=O)NH— | 3-isoquinolynyl |
| 147 | (R)—CH₂CH₂— | H | para-phenyl | —C(=O)NH— | 2-quinolynyl |
| 148 | (R)—CH₂CH₂— | H | para-phenyl | —C(=O)NH— | 2-naphthyl |
| 149 | (R)—CH₂CH₂— | H | para-phenyl | —C(=O)NH— | 3-quinolynyl |
| 150 | (R)—CH₂CH₂— | H | para-phenyl | —C(=O)NH— | 3-isoqinolynyl |
| 151 | (R)—CH₂CH₂— | H | para-phenyl | —C(=O)NH— | 2-quinolynyl |
| 152 | (R)—CH₂CH₂— | H | para-phenyl | —C(=O)NH— | 6-quinolynyl |
| 153 | (R)—CH₂CH₂— | H | para-phenyl | —C(=O)NH— | 3-quinoxalinyl |
| 154 | (R)—CH₂CH₂— | H | para-phenyl | —C(=O)NH— | 2-indolyl |
| 155 | (R)—CH₂CH₂— | H | para-phenyl | —C(=O)NH— | 5-chloro-2-indolyl |
| 156 | (R)—CH₂CH₂CH₂— | H | para-phenyl | —C(=O)NH— | 2-naphthyl |

| # | R⁶ | R⁷ | R⁸ |
|---|---|---|---|
| 1 | (L)(S)secBu | N—MeGly | Ile—NH₂ |
| 2 | (L)(S)secBu | —NHCH₂CH₂NHC(=O)— | CH₂-cyclopentyl |
| 3 | (L)(S)secBu | —NHCH₂CH₂—NHC(=O)— | n-Bu |
| 4 | (L)(S)secBu | N—MeGly | Ile—NH₂ |
| 5 | (L)(S)secBu | (D)Arg | Ile—NH₂ |
| 6 | (L)(S)secBu | (D)Arg | Ile—NH₂ |
| 7 | (L)(S)secBu | (D)Arg | Ile—NH₂ |
| 8 | (L)(S)secBu | (D)Arg | Ile—NH₂ |
| 9 | (L)(S)secBu | (D)Arg | Ile—NH₂ |
| 10 | (L)(S)secBu | (D)Arg | Ile—NH₂ |
| 11 | (L)(S)secBu | (D)Arg | Ile—NH₂ |
| 12 | (DL)(S)secBu | (L)Arg | Ile—NH₂ |
| 13 | (DL)(S)secBu | (D)Ornithine | Ile—NH₂ |
| 14 | (DL)(S)secBu | (D)Arg | Ile—NH₂ |
| 15 | (DL)(S)secBu | N—MeGly | Ile—NH₂ |
| 16 | (L)(S)secBu | (D)Arg | Ile—NH₂ |
| 17 | (DL)(S)secBu | (D)Arg | Ile—NH₂ |
| 18 | (DL)(S)secBu | N—MeGly | Ile—NH₂ |
| 19 | (L)(S)secBu | (D)Arg | Ile—NH₂ |
| 20 | (L)(S)secBu | (L)Arg | Ile—NH₂ |
| 21 | (L)(S)secBu | (L)Arg | Ile—NH₂ |
| 22 | (L)(S)secBu | (L)Arg | Ile—NH₂ |
| 23 | (L)(S)secBu | N—MeGly | Ile—NH₂ |
| 24 | (L)(S)secBu | Gly | Ile—NH₂ |
| 25 | (L)(S)secBu | N—MeGly | Ile—NH₂ |
| 26 | (L)(S)secBu | N—MeGly | Ile—NH₂ |
| 27 | (L)(S)secBu | N—MeGly | Ile—NH₂ |
| 28 | (L)(S)secBu | N—MeGly | Ile—NH₂ |
| 29 | (L)(S)secBu | N—MeGly | Ile—NH₂ |
| 30 | (L)(S)secBu | N—MeGly | Ile—NH₂ |
| 31 | (L)(S)secBu | N—MeGly | NH—I—Bu |
| 32 | (L)(S)secBu | N—MeGly | NH—I—Bu |
| 33 | (D)(S)secBu | (D)Arg | Ile—NH₂ |
| 34 | (D)isoBu | (L)Ornithine | NH—I—Bu |
| 35 | (D)isoBu | (D)Arg | Ile—NH₂ |
| 36 | (D)isoBu | N—MeGly | Ile—NH₂ |
| 37 | (D)isoBu | His | Ile—NH₂ |
| 38 | (D)isoBu | citrulline | NH—I—Bu |
| 39 | (D)isoBu | (D)Arg | NH—I—Bu |
| 40 | (L)(S)secBu | Pro | NH—I—Bu |
| 41 | (L)(S)secBu | Hyp | NH—I—Bu |
| 42 | (L)(S)secBu | 3-pyridinyl-Ala | NH—I—Bu |
| 43 | (L)(S)secBu | N—MeAla | NH—I—Bu |
| 44 | (L)(S)secBu | (D)N—MeAla | NH—I—Bu |
| 45 | (L)(S)secBu | aminobutyric acid | NH—I—Bu |
| 46 | (L)(S)secBu | thiazolidine | NH—I—Bu |
| 47 | (L)(S)secBu | Pro | Ile—NH₂ |
| 48 | (L)(S)secBu | Arg | (L)allo-Ile—NH₂ |
| 49 | (L)(S)secBu | (L)Ornithine | (L)allo-Ile—NH₂ |

-continued

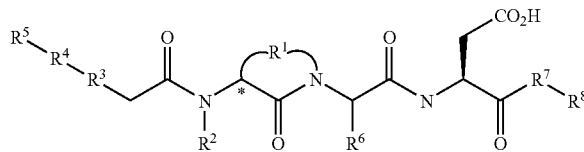

| | | | |
|---|---|---|---|
| 50 | (L)(S)secBu | (D)Ornithine | Ile—NH$_2$ |
| 51 | (L)(S)secBu | (D)Arg | Ile—NH$_2$ |
| 52 | (L)(S)secBu | (L)Ornithine | (D)Ile—NH$_2$ |
| 53 | (L)(S)secBu | Arg | (D)Ile—NH$_2$ |
| 54 | (L)(S)secBu | (D)Arg | NH—I—Bu |
| 55 | (L)(S)secBu | (D)Arg | Ile—NH$_2$ |
| 56 | (L)(S)secBu | (D)Arg | Ile—NH$_2$ |
| 57 | (L)(S)secBu | (D)Arg | Ile—NH$_2$ |
| 58 | (L)(S)secBu | (D)Ornithine | NH—I—Bu |
| 59 | (L)(S)secBu | (D)Arg | Ile—NH$_2$ |
| 60 | (L)(S)secBu | (D)Arg | Ile—NH$_2$ |
| 61 | (L)(S)secBu | (D)Arg | NH—I—Bu |
| 62 | (L)(S)secBu | (D)Arg | NH—I—Bu |
| 63 | (L)(S)secBu | (D)Arg | NH—I—Bu |
| 64 | (L)(S)secBu | (D)Arg | NH—I—Bu |
| 65 | (L)(S)secBu | (D)Arg | NH—I—Bu |
| 66 | (L)(S)secBu | N—MeGly | NH—I—Bu |
| 67 | (L)(S)secBu | N—MeGly | Ile—NH$_2$ |
| 68 | (L)(S)secBu | N—MeGly | Ile—NH$_2$ |
| 69 | (L)(S)secBu | N—MeGly | Ile—NH$_2$ |
| 70 | (L)(S)secBu | N—MeGly | Ile—NH$_2$ |
| 71 | (L)(S)secBu | N—MeGly | Ile—NH$_2$ |
| 72 | (L)(S)secBu | N—MeGly | Ile—NH$_2$ |
| 73 | (L)(S)secBu | N—MeGly | Ile—NH$_2$ |
| 74 | (L)(S)secBu | N—MeGly | Ile—NH$_2$ |
| 75 | (L)(S)secBu | N—MeGly | Ile—NH$_2$ |
| 76 | (L)(S)secBu | (D)Arg | Ile—NH$_2$ |
| 77 | (L)(S)secBu | N—MeGly | Ile—NH$_2$ |
| 78 | (L)(S)secBu | N—MeGly | Ile—NH$_2$ |
| 79 | (L)(S)secBu | (D)Ornithine | NH—I—Bu |
| 80 | (L)(S)secBu | (D)Arg | NH—I—Bu |
| 81 | (L)(S)secBu | (D)Arg | NH—I—Bu |
| 82 | (L)(S)secBu | Pro | NH—I—Bu |
| 83 | (L)(S)secBu | Pro | NH—I—Bu |
| 84 | (L)(S)secBu | Pro | NH—I—Bu |
| 85 | (L)(S)secBu | N—MeGly | NH—I—Bu |
| 86 | (L)(S)secBu | N—MeGly | Ile—NH$_2$ |
| 87 | (L)(S)secBu | (D)Ornithine | Ile—NH$_2$ |
| 88 | (L)(S)secBu | (D)Ornithine | Ile—NH$_2$ |
| 89 | (L)(S)secBu | (D)Ornithine | Ile—NH$_2$ |
| 90 | (L)(S)secBu | N—MeGly | Ile—NH$_2$ |
| 91 | (L)(S)secBu | (D)Ornithine | Ile—NH$_2$ |
| 92 | (L)(S)secBu | N—MeGly | Ile—NH$_2$ |
| 93 | (L)(S)secBu | N—MeGly | Ile—NH$_2$ |
| 94 | (L)(S)secBu | Arg | NH—I—Bu |
| 95 | (L)(S)secBu | NH-2-indolizidine | [n/a] |
| 96 | (L)(S)secBu | N—MeGly | —CH$_2$-2-THF |
| 97 | (L)(S)secBu | N—MeGly | (D)-t-BuGly—NH$_2$ |
| 98 | (L)(S)secBu | N—MeGly | (DL)-t-BuGly—NH$_2$ |
| 99 | (L)(S)secBu | N—MeGly | —NH-cycloleucinol |
| 100 | (L)(S)secBu | N—MeGly | —NH-2-(NHCH$_2$)-1-Et-pyrrolidine |
| 101 | (L)(S)secBu | N—MeGly | —NHCH$_2$-2-furan |
| 102 | (L)(S)secBu | N—MeGly | (D)-leucinol |
| 103 | (L)(S)secBu | N—MeGly | —NHCH$_2$-2-pyridinyl |
| 104 | (L)(S)secBu | Arg | Ile—NH$_2$ |
| 105 | (L)(S)secBu | Arg | Ile—NH$_2$ |
| 106 | (L)(S)secBu | Arg | Ile—NH$_2$ |
| 107 | (L)(S)secBu | Arg | Ile—NH$_2$ |
| 108 | (L)(S)secBu | Arg | Ile—NH$_2$ |
| 109 | (L)(S)secBu | Arg | Ile—NH$_2$ |
| 110 | (L)(S)secBu | Arg | Ile—NH$_2$ |
| 111 | (L)(S)secBu | Arg | Ile—NH$_2$ |
| 112 | (L)(S)secBu | Arg | Ile—NH$_2$ |
| 113 | (L)(S)secBu | Arg | Ile—NH$_2$ |
| 114 | (L)(S)secBu | Arg | Ile—NH$_2$ |
| 115 | (L)(S)secBu | Arg | Ile—NH$_2$ |
| 116 | (L)(S)secBu | Arg | Ile—NH$_2$ |
| 117 | (L)(S)secBu | Arg | Ile—NH$_2$ |
| 118 | (L)(S)secBu | Arg | Ile—NH$_2$ |
| 119 | (L)(S)secBu | Arg | (S)—NH-2-methylbutyl |

-continued

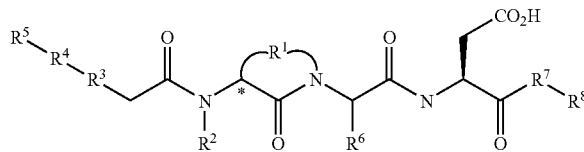

| | | | |
|---|---|---|---|
| 120 | (L)(S)secBu | Gly | (S)—NH-2-methylbutyl |
| 121 | (L)(S)secBu | Arg | —NH—CH$_2$-cyclohexyl |
| 122 | (L)(S)secBu | Gly | —NH—CH$_2$-cyclohexyl |
| 123 | (L)(S)secBu | (L)Arg | Ile—NH$_2$ |
| 124 | (L)(S)secBu | (L)Arg | Ile—NH$_2$ |
| 125 | (L)(S)secBu | (D)Arg | Ile—NH$_2$ |
| 126 | (L)(S)secBu | (D)Arg | Ile—NH$_2$ |
| 127 | (L)(S)secBu | N—MeGly | Ile—NH$_2$ |
| 128 | (L)(S)secBu | (D)Ornithine | Ile—NH$_2$ |
| 129 | (L)(S)secBu | (D)Ornithine | NH—I—Bu |
| 130 | (L)(S)secBu | (D)Arg | NH—I—Bu |
| 131 | (L)(S)secBu | N—MeGly | NH—I—Bu |
| 132 | (L)(S)secBu | (D)Arg | Ile—NH$_2$ |
| 133 | (L)(S)secBu | (D)Ornithine | Ile—NH$_2$ |
| 134 | (L)(S)secBu | N—MeGly | Ile—NH$_2$ |
| 135 | (L)(S)secBu | (D)Ornithine | Ile—NH$_2$ |
| 136 | (L)(S)secBu | N—MeGly | Ile—NH$_2$ |
| 137 | (L)(S)secBu | (D)Ornithine | Ile—NH$_2$ |
| 138 | (L)(S)secBu | (D)Arg | Ile—NH$_2$ |
| 139 | (L)(S)secBu | N—MeGly | Ile—NH$_2$ |
| 140 | (L)(S)secBu | (D)Ornithine | Ile—NH$_2$ |
| 141 | (L)(S)secBu | (D)Ornithine | —NH—I—Bu |
| 142 | (L)(S)secBu | (D)Ornithine | —NH—I—Bu |
| 143 | (L)(S)secBu | (D)Ornithine | —NH—I—Bu |
| 144 | (L)(S)secBu | (D)Ornithine | —NH—I—Bu |
| 145 | (L)(S)secBu | N—MeGly | —NH—I—Bu |
| 146 | (L)(S)secBu | N—MeGly | —NH—I—Bu |
| 147 | (L)(S)secBu | N—MeGly | —NH—I—Bu |
| 148 | (L)(S)secBu | (D)Arg | —NHCH$_2$-cyclohexyl |
| 149 | (L)(S)secBu | (D)Arg | —NHCH$_2$-cyclohexyl |
| 150 | (L)(S)secBu | (D)Arg | —NHCH$_2$-cyclohexyl |
| 151 | (L)(S)secBu | (D)Arg | —NHCH$_2$-cyclohexyl |
| 152 | (L)(S)secBu | (D)Arg | —NHCH$_2$-cyclohexyl |
| 153 | (L)(S)secBu | (D)Arg | —NHCH$_2$-cyclohexyl |
| 154 | (L)(S)secBu | (D)Arg | —NHCH$_2$-cyclohexyl |
| 155 | (L)(S)secBu | (D)Arg | —NHCH$_2$-cyclohexyl |
| 156 | (L)(S)secBu | Arg | —NH-isobutyl |

*when R$^1$ is imidazole, the central ring contains no carbonyl group

Administration and Uses

The compounds to be used in the present invention have been shown to specifically inhibit the activity of the natriuretic peptide clearance receptor, nprC. It has further been shown that inhibition of nprC leads to an increase in plasma levels and half-life of ANP, a potent non-catecholaminergic stimulator of lipolysis. It should be noted that the lipolytic effect of ANP is particular to humans and other human primates and is not seen in rodent or other mammalian model systems (Sengenes, et al., Am J Physiol Regul Integr Comp Physiol. 2002 July;283(1):R257-65). Thus, inhibition of nprC in humans will lead to increased levels of ANP, stimulating lipolysis and resulting in a decrease of adipose mass. Therefore, administration of nprC inhibitory compounds will be useful in the treatment of overweight and obesity as well as complications closely associated with obesity including but not limited to diabetes, atherosclerosis, coronary artery disease, cerebrovascular accident, transient ischemic accident, and cancer.

The present invention provides compositions comprising an effective amount of nprC inhibitory compounds, including the nontoxic addition of salts, amides and esters thereof, which may, serve to provide the above-recited therapeutic benefits. Such compositions can also be provided together with physiologically-tolerable liquid, gel or solid diluents, adjuvants and excipients. The compounds of the present invention may also be combined with other compounds known to be adjuvants for, or otherwise used as, therapeutic agents for the above or related indications.

These compounds and compositions may be administered to humans in a manner similar to other therapeutic agents. In general, the dosage required for therapeutic efficacy will range from about 0.01 to 1000 mg/Kg, more usually 0.1 to 100 mg/Kg of the host body weight. Alternatively, dosages within these ranges can be administered by constant infusion over an extended period of time until the desired therapeutic benefits have been obtained. Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%-2%. Oral formulations include such normally-employed excipients as, for example, pharmaceutical grades of mannitol, lactose, starch, magnesium stearate, sodium saccharin, cellulose, magnesium carbonate, and the like. These compositions take the form of solutions, suspensions tablets, pills, capsules, sustained-release formulations, or powders, and contain 10%-95% of active ingredient, preferably 25%-70%.

The peptide compounds may be formulated into compositions as neutral or salt forms. Pharmaceutically-acceptable nontoxic salts include the acid addition salts (formed with the free amino groups) and which are formed with inorganic acids such as for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of a peptide compound (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The compound may be administered once daily, preferably twice daily, more preferably thrice daily, more preferably weekly, and even more preferably monthly. In this example, the subject exhibits an increase in lipolysis in adipocytes and preferably exhibits a decrease in adipocyte mass and/or adipocyte cell number. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a peptide compound can include a single treatment or, preferably, can include a series of treatments.

In a preferred example, a subject is treated with a peptide compound in the range of between about 0.1 to 20 mg/kg body weight, one time per week for between about 1 to 30 weeks, preferably between 4 to 24 weeks, more preferably between about 8 to 20 weeks, and even more preferably for about 12, 15, or 18 weeks. It will also be appreciated that the effective dosage of antibody or polypeptide used for treatment may increase or decrease over the course of a particular treatment. Changes in dosage may result and become apparent from the results of diagnostic assays as described herein. A pharmaceutical composition of the invention is formulated to be compatible with its intended route of administration.

EXAMPLES

Example 1

An overweight/obese subject is administered an effective dose of a linear peptide nprC inhibitor and exhibits an increase in lipolysis resulting in a decrease in stored fat in adipocytes.

Example 2

An overweight/obese subject is administered an effective dose of a linear peptide nprC inhibitor and exhibits a decrease in nprC activity which results in an increase in lipolysis and a decrease of fat storage in adipocytes.

Example 3

An overweight/obese subject is administered an effective dose of a linear peptide nprC inhibitor and exhibits a decrease in adipose tissue mass.

Example 4

An overweight/obese subject is administered an effective dose of a linear peptide nprC inhibitor and exhibits a decrease in fat accumulation.

Example 5

An overweight/obese subject is administered an effective dose of a linear peptide nprC inhibitor and exhibits a decrease in adipocyte growth.

Example 6

An overweight/obese subject is administered an effective dose of a linear peptide nprC inhibitor and exhibits a decrease in body weight and an improved body mass index (BMI).

Examples of routes of administration include oral, parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Palo Alto, Calif.) and Alkermes (Cambridge Mass.). Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate parenteral compositions in "dosage unit form" for ease of administration and uniformity of dosage. "Dosage unit form", as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

In addition to the compounds of the present invention which display nprC inhibitory activity, compounds of the present invention may also be employed as intermediates in the synthesis of such useful compounds. Alternatively, by appropriate selection, compounds of the present invention whose activity levels are reduced or eliminated entirely can serve to modulate the activity of other nprC inhibitory compounds, including compounds outside the scope of the present invention, by, for example, binding to alternate receptors, stimulating receptor turnover, or providing alternate substrates for degradative enzyme or receptor activity and thus inhibiting these enzymes or receptors. When employed in this manner, such compounds may be delivered as admixtures with other active compounds or may be delivered separately, for example, in their own carriers.

Compounds of the present invention may also be used for preparing antisera for use in immunoassays employing labeled reagents, usually antibodies. Conveniently, the polypeptides can be conjugated to an antigenicity-conferring carrier, if necessary, by means of dialdehydes, carbodiimide or using commercially-available linkers. These compounds and immunologic reagents may be labeled with a variety of labels such as chromophores; fluorophores such as, e.g., fluorescein or rhodamine; radioisotopes such as 12'1, "s, "C, or 'H; or magnetized particles, by means well known in the art.

These labeled compounds and reagents, or labeled reagents capable of recognizing and specifically binding to them, can find use as, e.g., diagnostic reagents. Samples derived from biological specimens may be assayed for the presence or amount of substances having a common antigenic determinant with compounds of the present invention. In addition, monoclonal antibodies may be prepared by methods known in the art, which antibodies can find therapeutic use, e.g., to neutralize overproduction of immunologically-related compounds Synthesis The nprC inhibitory compounds to be used in the present invention may be chemically synthesized by methods well known to those of ordinary skill in the art and have been described in detail elsewhere (PCT International Publication No. WO 00/61631).

What is claimed is:

1. A method of reducing adipocyte growth in a subject comprising: (a) identifying an overweight or obese subject; and (b) administering to the subject so identified a therapeutically effective amount of a natriuretic peptide clearance receptor (nprC) inhibitor of the formula:

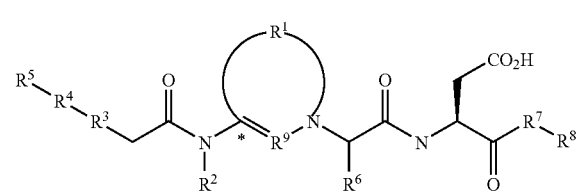

wherein
$R^1$ is —$CH_2CH_2$—, —$CH_2CH_2CH_2$—, =CH—CH=CH— or —N=CH—;
$R^2$ is H or $CH_3$ $R^3$ is —$CH_2CH_2CH_2$—, —(E)—CH=CHC(=O)NH—, —$CH_2CH_2$C(=O)NH—, para-disubstituted phenyl, ortho-disubstituted phenyl, or a single bond;

$R^4$ is —NHC(=O)—, —C(=O)NH—, or —S(=O)$_2$NH—;

$R^5$ is 1-naphthyl, 2-naphthyl, —$CH_2CH_2$NHCH$_2$CH=CH-phenyl, —$CH_2CH_2$-phenyl, —CH=CH-phenyl, 2-quinolyl, 3-quinolyl, 4-quinolyl, 6-quinolyl, 3-isoquinolyl, 2-quinoxaline, 5-chloro-2-indolyl, 2-indolyl, 4-chlorophenyl, 4-methylphenyl, 3-methoxyphenyl, 4-cyanophenyl, 3,4-difluorophenyl, 3-chloro-4-fluorophenyl, 2, 4-dichlorophenyl, 3,4-dichlorophenyl, 4-chlorophenyl, 3, 5-dimethoxyphenyl, 4-tert-butylphenyl, phenyl, 4-trifluoromethylphenyl, —$CH_2CH_2CH_2$-phenyl, 6-quinolyl-C(=O)—, 2-quinoxaline-C(=O)—, 5-chloro-2-benimidazolyl, fluorenylmethoxycarbonyl, 4-chlorobenzyl, 4-methylbenzyl, 3-quinoxalinyl, 3,4-difluorophenyl, or 4-fluuorophenyl;

$R^6$ is isobutyl or sec-butyl $R^7$ is N-methlyglycine, —NHCH$_2$CH$_2$NHC(=O)—, L-arginine, D-arginine, L-ornithine, D-ornithine, histidine, citrulline, proline, hydroxyproline, 3-pyridinylalanine, L-N-methylalanine, D-N-methylalanine, aminobutyric acid, N-2-indolizidinyl or thiazolidine;

$R^8$ is L-isoleucine-NH$_2$, D-isoleucine-NH$_2$, —CH$_2$-cyclopentyl, —CH$_2$-2-tetrahydrofuranyl, tert-butylglycine-NH$_2$, n-butyl, isobutyl, —NH-cyclopentyl, —NHCH$_2$-2-furanyl, —NHCH$_2$-pyrininyl, —NHCH$_2$-cyclohexyl, D-leucinol, —NH-isobutyl, L-allo-isoleucine-NH$_2$, 1-hydroxycycloleucinol, 2-(aminomethyl)-1-ethyl-pyrrolidine, or (S)—NH$_2$-methylbutyl or $R^8$ is absent when $R^7$ is N-2-indolizidinyl;

$R^9$ is =CH— or —C(=O)—; and

=* represents a double bond when $R^9$ is =CH— and a single bond when $R^9$ is C(=O)—.

2. The method of claim 1, wherein the subject is a mammal.

3. The method of claim 1, wherein the subject is a human.

4. The method of claim 1, wherein:

$R^1$ is —N=CH; and $R^9$ is =CH—.

5. The method of claim 1 wherein;

$R^1$ is —CH$_2$CH$_2$—, —CH$_2$CH$_2$CH$_2$—, or =CH—CH=CH—; and $R^9$ is —C(=O)—.

6. The method of claim 5, wherein, $R^2$ is H;

$R^5$ is 2-quinoxaline;

$R^7$ is L-arginine or D-arginine; and $R^8$ is L-isoleucine-NH$_2$ or D-isoleucine-NH$_2$.

7. The method of claim 5, wherein, $R^1$ is —CH$_2$CH$_2$—;

$R^3$ is a para-disubstituted phenyl;

$R^4$ is —C(=O)NH—;

$R^5$ is is 1-naphthyl, 2-naphthyl, —CH$_2$CH$_2$NHCH$_2$CH=CH—phenyl, —CH$_2$CH$_2$-phenyl, —CH=CH-phenyl, 2-quinolyl, 3-quinolyl, 4-quinolyl, 6-quinolyl, 3-isoquinolyl, 2-quinoxaline, 5-chloro-2-indolyl, 2-indolyl, 4-chlorophenyl, 4-methylphenyl, 3-methoxyphenyl, 4-cyanophenyl, 3,4-difluorophenyl, 3-chloro-4-fluorophenyl, 2,4-dichlorophenyl, 3,4-dichlorophenyl, 4-chlorophenyl, 3,5-dimethoxyphenyl, 4-tert-butylphenyl, phenyl or 4-trifluorophenyl; and $R^6$ is sec-butyl.

8. The method of claim 1, wherein the nprC inhibitor is administered as a pharmaceutical composition in an effective dosage ranging from about 0.001 to 30 mg/kg body weight.

9. The method of claim 8, wherein the pharmaceutical composition of the nprC inhibitor is administered in an effective dosage ranging from about 0.01 to 25 mg/kg body weight.

10. The method of claim 9, wherein the pharmaceutical composition of the nprC inhibitor is administered in an effective dosage ranging from about 0.1 to 20 mg/kg body weight.

11. The method of claim 10, wherein the pharmaceutical composition of the nprC inhibitor is administered in an effective dosage ranging from about 1 to 10 mg/kg body weight.

12. The method of claim 1, wherein the nprC inhibitor is administered once daily.

13. The method of claim 1, wherein the nprC inhibitor is administered once monthly.

* * * * *